United States Patent
Christ et al.

(10) Patent No.: US 7,309,609 B2
(45) Date of Patent: Dec. 18, 2007

(54) DETECTION OF OXIDATION OF CARBON-CONTAINING FIBERS OR FIBER BUNDLES IN COMPOSITES

(75) Inventors: Martin Christ, Wehringen (DE); Michael Heine, Allmannshofen (DE)

(73) Assignee: SGL Carbon AG (DE)

( * ) Notice: Subject to any disclaimer, the term of this patent is extended or adjusted under 35 U.S.C. 154(b) by 717 days.

(21) Appl. No.: 10/624,697

(22) Filed: Jul. 22, 2003

(65) Prior Publication Data
US 2004/0124087 A1 Jul. 1, 2004

(30) Foreign Application Priority Data
Jul. 30, 2002 (DE) .............................. 102 34 551

(51) Int. Cl.
G01N 25/18 (2006.01)
G01N 27/00 (2006.01)
G01R 31/26 (2006.01)
G01R 31/28 (2006.01)
H01L 23/58 (2006.01)
H01L 29/10 (2006.01)

(52) U.S. Cl. .......................... 436/149; 438/17; 438/18; 257/48; 324/158.1

(58) Field of Classification Search ..................... None
See application file for complete search history.

(56) References Cited

U.S. PATENT DOCUMENTS 4,924,182 A   5/1990   Vernon et al.
5,438,262 A   8/1995   Nanjyo et al.
5,725,955 A   3/1998   Tawil et al.

FOREIGN PATENT DOCUMENTS

| DE | 199 45 944 A1 | 5/2001 |
| DE | EP 1 241 473 A1 * | 9/2002 |
| EP | 0 619 801 B1 | 10/1994 |

OTHER PUBLICATIONS

"Non Destructive Inspection for Carbon-Carbon With Adapted Coating for Oxidation"; Aerospatiale; P. Plotard et al; A-25, pp. 1-9; Apr. 1991.

"Non-Destructive Characterization of SiC coated Carbon-Carbon Composites by Multiple Techniques"; T. D. Nion, S. N. Hemstad, W. H. Pfeifer; 24th International Sampe Technical Conference; pp. T13-T27; 1992.

\* cited by examiner

*Primary Examiner*—Jill Warden
*Assistant Examiner*—Keri A Moss
(74) *Attorney, Agent, or Firm*—Connolly Bove Lodge & Hutz LLP

(57) ABSTRACT

The invention relates to the detection of oxidation of carbon-containing fibers or fiber bundles embedded in a nonconductive or semiconducting ceramic matrix in composites wherein use is made of the eddy current method.

6 Claims, 1 Drawing Sheet

DETECTION OF OXIDATION OF CARBON-CONTAINING FIBERS OR FIBER BUNDLES IN COMPOSITES

FIELD OF THE INVENTION

The invention relates to a process for the detection of oxidation of carbon-containing fibers or fiber bundles in composites as claimed in claim 1.

BACKGROUND OF THE INVENTION

In EP 0 619 801 B1 it is stated as a problem that the carbon in composites having a ceramic matrix and reinforced with carbon fibers, for example C/SiC materials (carbon-silicon carbide), tends to oxidize, especially in applications at a relatively high temperature. This behavior is a particular disadvantage if shaped bodies used in a high-temperature environment, for example brake disks of vehicles, are made of the carbon-containing material. In the case of such brake disks, undesirable oxidation of the carbon fibers has in the past been observed at operating temperatures of from about 700° C. to 1000° C. As combustion or oxidation of the carbon fibers progresses, structural damage to the brake disk which has an adverse effect on its stiffness and strength may occur. In view of the expensive manufacture of such fiber-reinforced C/SiC brake components, replacement on the basis of need rather than as a precaution is preferable. However, this requires regular nondestructive testing of the brake components.

Attempts have been made in the past to determine a loss of carbon caused by oxidation by weighing components made of the abovementioned composites. However, this method is very costly since it requires removal of the C/SiC component from the assembly. Furthermore, such components were subjected to optical inspection. Although this method enables conclusions regarding the surface state of the C/SiC component to be drawn readily, it is only suitable for assessing the overall state of the component if the surface state corresponds exactly with the state of the remaining component. This is reliable enough only in very rare cases.

SUMMARY OF THE INVENTION

Accordingly, it is an object of the invention to provide a reliable, nondestructive method of detecting oxidation of carbon-containing fibers in the composites mentioned above which is simple to carry out and precise.

This object is achieved according to the invention by the features of claim 1.

According to the invention, oxidation of carbon-containing fibers or fiber bundles is detected using the eddy current method which is known per se and is described, for example, in DE 199 45 944 A1. However, application of this method to composites having a nonconductive or semiconducting ceramic matrix initially appears unpromising because of their limited induction capability. Furthermore, the oxidation of the carbon fibers does not result in cracks as are formed by mechanical stress and are known as a typical application of the eddy current method.

Unlike the case of the prior art, the eddy current method is applied not to a material which is homogeneous in terms of its electrical conductivity but to a composite in which material having a good electrical conductivity (carbon-containing fibers) is combined with a nonconductive or semiconducting material (ceramic matrix). The application of the eddy current method to composites having such properties has the surprising and advantageous consequence that oxidation of the carbon fibers results in a drastic change in the output signal of the eddy current method compared to a reference material which has not been affected by oxidation. This is because the electrical conductor necessary for induction of the eddy currents, namely the carbon-containing fibers, are partly or completely destroyed by oxidation, which has a particularly strong effect on the output signal. Consequently, the eddy current method which is known per se is significantly more sensitive, more accurate and more reliable when applied to the composites mentioned.

DETAILED DESCRIPTION OF THE PREFERRED EMBODIMENTS

Furthermore, it is possible to detect oxidation of the carbon-containing fibers even in deeper layers of the composite, because the fibers or fiber bundles, in the composite which is reinforced by means of short fibers, are randomly distributed in the nonconductive or semiconducting matrix and are thus effectively electrically insulated from one another. As a result, the "skin effect" does not occur in the composite when the eddy current method is applied according to the invention to the composites mentioned. If the eddy current method is applied to materials having a homogeneous electrical conductivity, this effect occurs and defects are detected only in the surface layer of the material. The carbon-containing fibers are electrically conducting and usually have a diameter of from 5 μm to 12 μm, preferably of from 6 μm to 10 μm. They are short fibers with a length from 0.1 mm to 30 mm, preferably from 0.2 mm to 5 mm. During the oxidation of the fibers, they are attacked on their surfaces, with the oxidative attack being approximately uniform throughout the fiber surface.

The ceramic matrix is preferably present in at least the surface layer of the composite and comprises silicon carbide (SiC) together with silicon (Si) and/or silicon alloys. The eddy current method is therefore preferably applied to fiber-reinforced C/SiC materials in which carbon-containing fibers, in particular carbon fibers or graphite fibers, are present in a matrix comprising predominantly SiC and Si. The C/SiC composite ceramics can further comprise fibers comprising carbon together with further elements such as Si, B, N, P or Ti. These fibers are resistant to high temperatures and have a significantly higher electrical conductivity than the preferably nonconductive or semiconducting matrix. While the resistivity of the carbon-containing fibers is approximately 1 μΩ·m to 10 μΩ·m, that of silicon (Si) is approximately 1000 μΩ·m, and that of silicon carbide (SiC) is approximately $10^6$ μΩ·m to $10^7$ μΩ·m. The composites referred to herein usually have a resistivity of from about 30 μΩ·m to about 400 μΩ·m. In the following and in the claims, the term fibers encompasses both individual fibers and fiber bundles which may be bound together by means of polymers or their pyrolysis products, preferably graphitic carbon. The fibers or fiber bundles are randomly distributed in the matrix and electrical conduction between the dispersed fibers or fiber bundles is restricted by the non-conducting or semiconducting matrix. Fiber bundles, for the purposes of the present invention, are an agglomerate of short fibers in substantially parallel direction, comprising from about 500 to about 20,000, preferably from about 1000 to about 10,000 individual fibers.

In the production of C/SiC material, a CFRC material is formed first. Particular preference is given to producing a CFRP (carbon fiber-reinforced polymer) reinforced with short fiber bundles and comprising carbon fibers or fiber bundles coated with a carbonizable substance and/or with carbon and also fillers and binders, which is pressed, if appropriate with the aid of a pressing core, to give the desired shape and is cured and then carbonized and/or graphitized to form a shaped CFRC or C/C body as intermediate. Since the CFRP and CFRC intermediates still have a relatively low hardness compared to the future composite ceramic, cutting machining procedures, for example drilling of holes or milling, are preferably carried out on these intermediates.

The preferred shaped body made of carbon fiber-reinforced carbon (CFRC) is subsequently machined to bring it close to its final shape and then infiltrated with a silicon melt or a silicon alloy melt at temperatures of about 1600° C. under reduced pressure or under inert gas, which results in conversion of at least part of the carbon of the matrix and/or the fibers into SiC. Apart from silicon, further constituents which can be present in the melt are boron (B) and the metals of transition groups I to VIII, in particular Ti, Cr, Fe, Mo, and Ni. The liquid infiltration of the shaped CFRC body forms a dense, strong and very hard shaped body of C/SiC material comprising fibers, generally carbon fibers, in a matrix of predominantly SiC and Si.

As an alternative, the matrix of the shaped body can be produced entirely or partly by chemical vapour deposition or gas-phase infiltration (CVD or CVI). The matrix then has a relatively high SiC content, typically above 95%. Furthermore, production of the matrix can be carried out by pyrolysis of Si-containing, preceramic polymers, for example by pyrolysis of polymers comprising one or more of the elements Si, B, C, N, P or Ti.

The shaped C/SiC bodies are preferably brake disks, brake linings or clutch disks. However, owing to the good heat resistance, any other application in which high temperatures occur is conceivable, for example as linings for furnaces and combustion chambers or as heat shields, in particular in engine or nozzle construction.

In each of the three cases, the shaped composite body produced in the respective processes therefore comprises a composite ceramic having carbon-containing fibers embedded in a nonconductive or semiconducting matrix of SiC and Si. For the purposes of the invention, Si is a semiconductor and SiC is an insulator (nonconductive material). This applies particularly to the temperatures which are preferred for the measurement and are far below the maximum use temperature of the components. Alternatively, the matrix could also comprise a further electrically nonconductive material, for example TiC, TiC/SiC, $Si_3N_4$, $SiC/Si_3N_4$ or $Al_2O_3$.

The SiC content of the composite ceramic is preferably above 25% by weight, particularly preferably above 50% by weight, based on the total weight of the shaped body. Depending on the depth of infiltration with the matrix-forming compounds, this composite ceramic can be restricted to a surface layer or can extend through the entire shaped body. The proportion by weight of the matrix and its composition can vary within the shaped body, particularly deep inside, with the proportion by weight of matrix at the surface preferably being higher than in the interior of the shaped body and being able to be virtually 100%.

In a preferred variant, the CFRC material is converted into C/SiC by liquid silicization. Here, it is unimportant whether the CFRC material is entirely or only partly infiltrated with silicon or silicon alloy and converted into C/SiC. It is only necessary for the surface layer of the shaped body to have been converted into C/SiC, and this can also comprise virtually 100% of matrix, in particular SiC. Shaped CFRC bodies in which silicization has been carried out only in the surface region and the core of CFRC remains are also used. The thickness of the surface layer which has been converted into C/SiC is at least 0.2 mm, preferably more than 0.5 mm and particularly preferably more than 5 mm.

After cooling of the material from a process temperature of about 1500 to 1900° C. to room temperature, the liquid silicization of CFRC leads, owing to the different coefficients of thermal expansion of fibers and matrix, to a matrix containing open microcracks and pores which extend far into the interior of the shaped C/SiC ceramic body and are formed preferentially at the carbon-containing reinforcing fibers. This likewise applies to the gas-phase infiltration or polymer pyrolysis processes, since in these cases, too, the body is cooled from a high process temperature to low temperatures. This effect occurs particularly when the SiC-containing surface layer has a higher proportion by weight of matrix than does the interior of the material.

These open cracks and pores form paths for oxygen to penetrate the body, so that, in particular, the carbon-containing fibers bound in the matrix are exposed to oxidation. Use of the shaped body in the high temperature range and in corrosive media, as are customary for such materials, further increases oxidative attack. As has been mentioned at the outset, brake disks of vehicles, inter alia, are manufactured from the C/SiC material and these components can reach temperatures above 700° C. in operation, so that such components in particular are exposed to oxidative and structure-damaging attack. In this safety component, knowledge of the precise state of the material is of particular importance.

According to the invention, the eddy current method which is known per se, for example from DE 199 45 944 A1 where it is used for the nondestructive detection of cracks in electrically conductive material, is used for detecting oxidation of the carbon-containing fibers or fiber bundles. In the eddy current method, electric eddy currents are induced in electrically conductive materials by means of an induction coil through which high-frequency current flows. The eddy currents occurring in the material are measured by means of a testing coil of a detector, for example as the induced voltage which is proportional to the magnetic flux density produced by the eddy currents. It is also possible to use a magnetometer provided with a testing coil for measuring the amplitude of the flux density or a gradiometer by means of which the gradient of the flux density generated is measured as detector. Changes in the magnetic field or the induced voltage in the testing coil indicate the presence of defects in the material.

The measurement is preferably carried out by a noncontact method. The opportunity of a noncontact measurement is particularly advantageous when the testing intervals do not permit complete cooling of the high-temperature components. In the present case, this method is applied to shaped bodies made of the above-described composite. A use example is described below and illustrated by the FIGURE, which shows an apparatus for application of the eddy current method to a brake disk in the installed state in a highly schematic manner.

DESCRIPTION OF THE DRAWING

In the FIGURE, a primary or induction coil to which a primary voltage $U_p$ is applied and through which a high-frequency current flows is denoted by 1. As a result, a magnetic AC field is generated in a shaped body, preferably a brake disk 2 made of a C/SiC composite ceramic containing embedded carbon fibers and this induces electric eddy currents in the carbon fibers. For reasons of scale, only a section of the brake disk 2 is shown in the FIGURE. The primary coil 1 preferably has its central axis vertical and is preferably located with its end face in direct proximity to the outer surface of the brake disk 2.

The eddy currents in turn induce a current through a secondary coil 4, which produces a secondary voltage $U_s$. The secondary coil 4 is preferably located on the same side of the brake disk 2 as the primary coil 1 and is surrounded by the latter. To determine the extent of oxidation of the carbon fibers of the brake disk 2, it is possible to employ either the absolute value of the secondary voltage $U_s$ or the phase shift between this and the primary voltage $U_p$.

Figure 1:
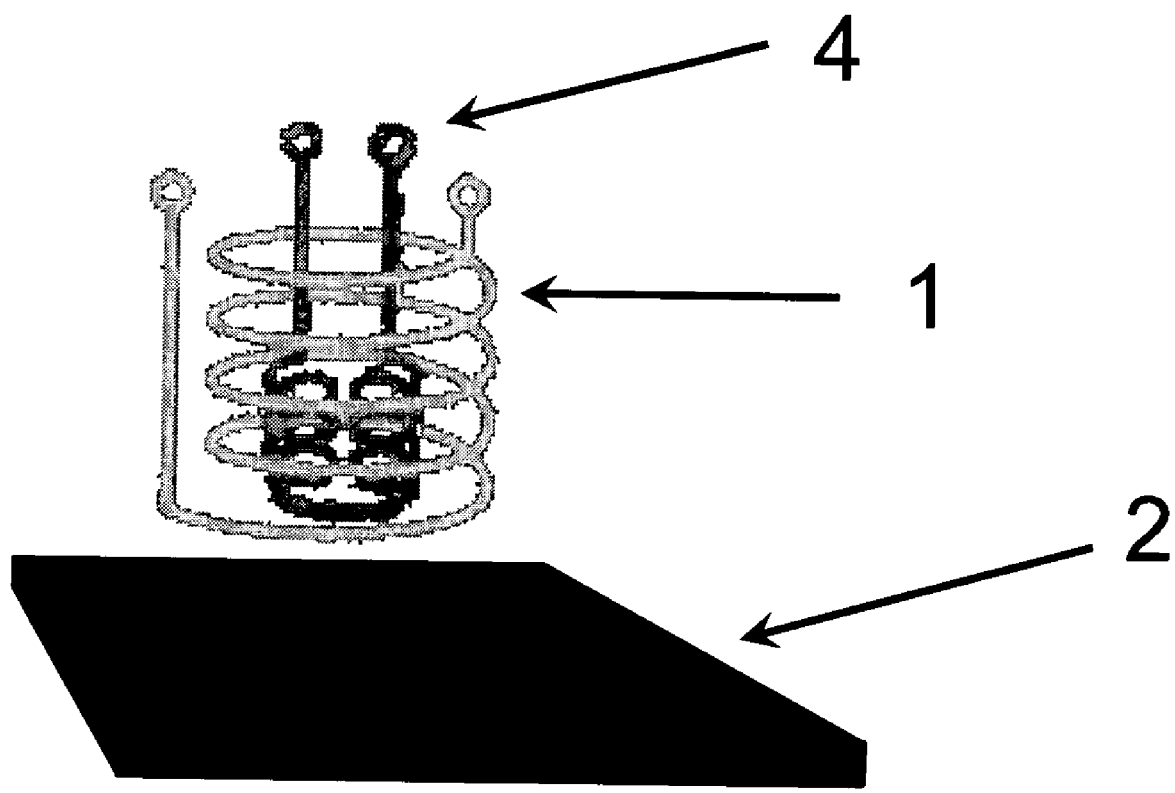

The invention claimed is:

1. A method of detection of oxidation of carbon-containing fibers or fiber-bundles in composites which are fiber-reinforced C/SiC materials in which carbon fibers or graphite fibers are present in a ceramic matrix comprising predominantly SiC and Si, using the eddy current method, wherein the said composites consist of carbon or graphite fibers or fiber bundles and a non-conducting or semi-conducting ceramic matrix, and wherein the said fibers or fiber bundles are electrically conducting short fibers isolated by the said non-conducting or semiconducting ceramic matrix such that the fibers or fiber bundles are effectively electrically insulated and there is no skin effect upon electrical induction, comprising applying an alternating magnetic field to the composite, the eddy current generated within the fibers causing a signal which is markedly different for oxidated fibers and non-oxidated fibers.

2. The method of claim 1, wherein an eddy current is generated in the fibers of a body made of a composite as claimed in claim 1 in which the said non-conducting or semi-conducting ceramic matrix is present in at least a surface layer of the said body.

3. The method of claim 2, wherein the eddy current is generated in the fibers of the said body in which the ceramic matrix in at least the surface layer comprises SiC as main constituent and Si and/or Si alloys as further phases.

4. The method of claim 1, wherein the eddy current is generated in the fibers of a composite which fibers are short fibers having a diameter of from 5 μm to 12 μm, and a length of from 0.1 mm to 30 mm.

5. The method of claim 1, wherein the eddy current is generated in the fibers of a composite, comprising measuring the signal in a configuration where an induction coil (1) and a testing coil (4) are arranged on the same side of a shaped body (2) made of the composite.

6. The method of claim 1, wherein the eddy current is generated in the fibers of a composite material that can be subjected to high thermal load.

* * * * *